(12) United States Patent
Biniwale et al.

(10) Patent No.: US 9,005,571 B2
(45) Date of Patent: Apr. 14, 2015

(54) PROCESS FOR THE STORAGE DELIVERY OF HYDROGEN USING CATALYST

(71) Applicants: Rajesh Bhaskar Biniwale, Nagpur (IN); Jayshri Vijay Pande, Nagpur (IN); Anshu Ajit Shukla, Nagpur (IN)

(72) Inventors: Rajesh Bhaskar Biniwale, Nagpur (IN); Jayshri Vijay Pande, Nagpur (IN); Anshu Ajit Shukla, Nagpur (IN)

(73) Assignee: Council of Scientific & Industrial Research (IN)

( * ) Notice: Subject to any disclaimer, the term of this patent is extended or adjusted under 35 U.S.C. 154(b) by 72 days.

(21) Appl. No.: 13/750,722

(22) Filed: Jan. 25, 2013

(65) Prior Publication Data
US 2013/0142726 A1 Jun. 6, 2013

Related U.S. Application Data

(63) Continuation of application No. PCT/IN2011/000492, filed on Jul. 26, 2011.

(30) Foreign Application Priority Data

Jul. 26, 2010 (IN) .......................... 1739/DEL/2010

(51) Int. Cl.
*C01B 3/26* (2006.01)
*C01B 3/32* (2006.01)
(Continued)

(52) U.S. Cl.
CPC .................. *C01B 3/326* (2013.01); *B01J 21/18* (2013.01); *B01J 23/42* (2013.01); *B01J 23/464* (2013.01);
(Continued)

(58) Field of Classification Search
CPC .................................. C01B 3/326; B01J 23/42

USPC ................................................... 423/650, 651
See application file for complete search history.

(56) References Cited

U.S. PATENT DOCUMENTS 3,138,433 A  6/1964  Del Giudice
3,223,617 A  12/1965  Maziuk
(Continued)

FOREIGN PATENT DOCUMENTS

FR      2860455 A1   4/2005
JP    2001110437 A   4/2001
(Continued)

OTHER PUBLICATIONS

Pradhan, et al.; "A Feasibility Analysis of Hydrogen Delivery System Using Liquid Organic Hydrides"; International Journal of Hydrogen Energy; 2011; pp. 680-688.
(Continued)

*Primary Examiner* — Paul Wartalowicz
(74) *Attorney, Agent, or Firm* — St. Onge Steward Johnston & Reens, LLC

(57) ABSTRACT

Hydrogenated liquid organic compounds are used for storage and supply of hydrogen at near ambient conditions. The hydrogen is released from the hydrogenated liquid organic compounds through a catalytic dehydrogenation reaction using a M/support or M-M'/support catalyst. The M/support catalyst comprises a metal M selected from Pt, Pd, Rh, Ru, Ir, Os, or combination thereof, and a support selected from $Y_2O_3$ or $V_2O_5$ or combinations thereof. The M-M'/support catalyst comprises a first metal M selected from Cu, Ag, Au, or combination thereof, a second metal M' selected from Pt, Pd, Rh, Ru, Ir, Os, Fe, Ni, Re, Mo, W, V, Cr, Co or combinations thereof, and a support selected from activated carbon, alumina, alumite, zirconia, silica or combination thereof. Synergistic effects are created by using the combination of the M and M' in the catalyst, which result in shifting of the equilibrium of the reaction favorably to dehydrogenation.

15 Claims, 3 Drawing Sheets

(51) Int. Cl.
*B01J 23/42* (2006.01)
*B01J 23/46* (2006.01)
*B01J 23/50* (2006.01)
*B01J 23/63* (2006.01)
*B01J 23/648* (2006.01)
*B01J 23/66* (2006.01)
*B01J 35/06* (2006.01)
*B01J 37/02* (2006.01)
*C07C 5/32* (2006.01)
*H01M 8/06* (2006.01)
*B01J 21/18* (2006.01)

(52) U.S. Cl.
CPC B01J 23/50 (2013.01); B01J 23/63 (2013.01); B01J 23/6482 (2013.01); B01J 23/66 (2013.01); B01J 35/06 (2013.01); B01J 37/0211 (2013.01); C01B 3/26 (2013.01); C07C 5/325 (2013.01); H01M 8/065 (2013.01); *Y02E 60/50* (2013.01)

(56) References Cited

U.S. PATENT DOCUMENTS

| | | | |
|---|---|---|---|
| 3,759,823 A | 9/1973 | Davies et al. | |
| RE29,597 E * | 3/1978 | Brownstein et al. | 549/518 |
| 4,171,243 A * | 10/1979 | Brooks et al. | 159/48.1 |
| 4,206,186 A * | 6/1980 | Holter et al. | 423/230 |
| 4,349,450 A * | 9/1982 | Hunter | 502/334 |
| 4,478,814 A * | 10/1984 | Kesten et al. | 423/650 |
| 4,567,033 A | 1/1986 | Kesten | |
| 4,886,928 A * | 12/1989 | Imai et al. | 585/660 |
| 5,198,207 A | 3/1993 | Knott et al. | |
| 5,372,617 A | 12/1994 | Kerrebrock et al. | |
| 5,702,491 A | 12/1997 | Long et al. | |
| 5,833,934 A | 11/1998 | Adlhart | |
| 6,074,447 A | 6/2000 | Jensen | |
| 6,781,024 B2 * | 8/2004 | Butler et al. | 585/440 |
| 6,802,875 B1 | 10/2004 | Kimbara et al. | |
| 7,101,530 B2 | 9/2006 | Pez et al. | |
| 2001/0014309 A1 | 8/2001 | Zaluska et al. | |
| 2003/0014917 A1 | 1/2003 | Rusta-Sallehy et al. | |
| 2003/0053948 A1 | 3/2003 | Bogdanovic et al. | |
| 2003/0091876 A1 | 5/2003 | Rusta-Sellehy et al. | |
| 2003/0091879 A1 | 5/2003 | Rusta-Sellehy et al. | |
| 2003/0099595 A1 | 5/2003 | Yebka et al. | |
| 2004/0074759 A1 | 4/2004 | Purta et al. | |
| 2004/0199039 A1 * | 10/2004 | Brophy et al. | 585/660 |
| 2005/0002857 A1 | 1/2005 | Pez et al. | |
| 2005/0013767 A1 | 1/2005 | Bagzis et al. | |
| 2005/0032641 A1 | 2/2005 | Zidan et al. | |
| 2006/0143981 A1 | 7/2006 | Toseland et al. | |
| 2009/0025824 A1 | 1/2009 | Noujima et al. | |
| 2009/0177020 A1 * | 7/2009 | Suzuki et al. | 585/407 |
| 2010/0010280 A1 | 1/2010 | Fridman | |
| 2011/0053020 A1 * | 3/2011 | Norton et al. | 429/425 |

FOREIGN PATENT DOCUMENTS

| | | |
|---|---|---|
| JP | 2001198469 A | 7/2001 |
| JP | 2002134141 A | 5/2002 |
| WO | 9703919 A1 | 2/1997 |
| WO | 9902422 A1 | 1/1999 |

OTHER PUBLICATIONS

International Preliminary Report on Patentability Application No. PCT/IN2011/000492 Completed: Nov. 7, 2012 25 pages.

International Search Report & Written Opinion of the International Searching Authority Application No. PCT/IN2011/000492 Completed: Nov. 30, 2011; Mailing Date: Mar. 13, 2012 15 pages.

* cited by examiner

PROCESS FOR THE STORAGE DELIVERY OF HYDROGEN USING CATALYST

FIELD OF THE INVENTION

The present invention relates to improved process for storage and delivery of hydrogen by dehydrogenation of hydrogenated liquid organic compounds through dehydrogenation reaction over catalysts with general formula M/support and M-M'/support where M and M' are metals. The present invention further relates to use of pure hydrogen for hydrogen storage, transportation and delivery using hydrogenated liquid organic compounds for utilization in fuel cell applications including mobile and stationary application and any other application wherein pure hydrogen is required. The other applications may include hydrogen supply to vegetable oil industry, glass industry etc.

BACKGROUND OF THE INVENTION

Hydrogen is being pursued as clean fuel for future applications particularly, by using fuel cells, in transportation sector. Four major issues need to be addressed for hydrogen energy utilization include; production of hydrogen, delivery to fueling station, onboard storage on vehicle and utilization of hydrogen for power generation. Hydrogen storage and supply is therefore an important aspect of successful utilization of hydrogen energy. Presently several methods used for hydrogen storage include, pressurization, liquefaction, physical adsorption on various adsorbents including carbon nanotubes, metal hydrides, alanates, hybrid hydrides and chemical hydrides. All these methods of hydrogen storage except chemical hydrides besets with disadvantage that either a particular method is having low weight basis capacity of hydrogen storage or volumetric capacity is lower.

Hydrogen containing chemicals which are useful for storage of hydrogen include methanol, ammonia and cycloalkanes. At standard temperature and pressure all these are in liquid phase and therefore provide advantage of possibility of using existing infrastructure used for gasoline. The hydrogen storage capacities of these may range in the scale of 6 to 8 wt %. The supply of hydrogen through liquid organic hydrides (LOH) using catalytic reaction pair of dehydrogenation of cycloalkanes such as methylcyclohexane, cyclohexane and decalin; and hydrogenation of corresponding aromatics would be a useful process for supply of hydrogen to PEM (proton exchange membrane) fuel cells and is expected to overcome the disadvantages of other hydrogen storage systems. This would be the most promising methods to store, transport and supply with in-situ generation of hydrogen due to several advantages associated with this system which include; CO free hydrogen at fuelling stations, reversible catalytic reactions, recyclable reactants and products, relatively high hydrogen contents (6-8% on weight basis and about 60-62 kg $H_2/m^3$ on volume basis) and no $CO_2$ generation as in the case of steam reforming of hydrocarbons. Due to high boiling points of cycloalkanes, the present infrastructure such as oil tankers and tank lorries can be used for the long-term storage and long-distance transportation of hydrogen in the form of LOH. Particularly, the approach is expected to be most useful to transport the hydrogen from centralized generation facilities to fuelling stations.

Reference may be made to U.S. Pat. No. 5,198,207, wherein doping of magnesium with other metals such as aluminium, indium, iron, etc. has been used to catalyze the hydrogenation of magnesium. U.S. Pat. No. 5,198,207 suggests adding to the magnesium a small amount of magnesium hydride, typically higher than 1.2% by weight, in order to catalyze the hydrogenation of magnesium at temperatures above 250° C. under a pressure ranging between 5 and 50 bars. According to what is disclosed in the patent, this technique called "autocatalysis" permits to complete the hydrogenation in a period of time longer than 7 hours. The drawback of this method is requirement of relatively high pressures for hydrogenation.

Reference may be made to Patent Application US20010014309, wherein a hydrogen storage composition having a hydrogenated state and a dehydrogenated state has been described; the hydrogenated state comprises a hydride composition of lithium and an element M which forms a hydride, for example Be or Mg, an element which forms a compound or solid solution with lithium, e.g. C, B or Zn, or a mixture thereof; there are thus provided reversible Li-based hydrides of high hydrogen capacity. The drawback of this method is that longer equilibrium periods are required. This drawback has been overcome in this invention by using instantaneous catalytic reaction for hydrogenation and dehydrogenation.

Several patents describe the inventions related to Mg-based alloys for storage of hydrogen. Reference maybe made to International patent application WO 99/2422, wherein a process for the preparation of a nano-composite for the storage of hydrogen comprising the step of subjecting to an intensive mechanical grinding a magnesium hydride or an hydride of a Mg-based compound and one or more elements or compounds that are known to absorb hydrogen and to be not miscible with magnesium during grinding is disclosed. Indeed, this process requires the use of magnesium hydride as starting material. The drawback of this method is relatively low capacity for hydrogen and long mixing times for equilibrium.

Use of alanates has been reported for hydrogen storage. Reference maybe made to Patent Application No US20030053948, Patent application PCT/WO 97/03919, U.S. Pat. No. 3,138,433 and Patent Application No US20050032641, wherein alanates have been used for hydrogen storage. The drawbacks of these methods are that the hydrogen capacity of all these methods described are relatively low and requires longer time of equilibrium for hydrogenation.

Reference may be made to U.S. Pat. No. 3,759,823, which describes a hydrocarbon conversion catalysts of 0.01-10% wt metal on a refractory support contains platinum and a second metal which forms a solid with Pt, the atomic amount of each being equivalent to amounts forming ordered alloy structures. The second metal may be Co, Ni, Fe, Cu, Sn, Pd, or Cd and preferably there is at least 45 atomic percent Pt. the catalysts may be prepared by known impregnation or ion exchange techniques and are preferably reduced before use at 250-600° C. The preferred use is dehydrocyclisation or dehydrogenation of C3-C25 hydrocarbons, particularly the catalytic reforming of 15-204° C., boiling range petroleum fractions.

Reference may be made to U.S. Pat. No. 4,567,033, which describes a method "freeing" molecular hydrogen from methylcyclohexane by its dehydrogenation to toluene at 316° C. The required thermal input being supplied by combustion of a considerable portion of the by-product hydrogen.

Reference maybe made to U.S. Pat. No. 5,372,617, which describes an invention related to a type of hydrogen generation system wherein chemical hydrides in solid phase are used, e.g. granules, comprises a closed vessel for mixing chemical hydride powder together with water. The water is introduced into the vessel through an inlet. The vessel contains a mechanical stirring device to ensure adequate contact between the powder and the water, and to prevent the powder from clumping. The hydrogen gas is removed through an outlet in the vessel, and is supplied directly to the fuel cell. These systems tend to be inefficient since the stirring mechanism consumes energy, and increases the overall weight and complexity of the system. The reaction rate tends to be low, making the hydrogen generation unpredictable and thus hard to control. The systems also tend to be large and cumbersome.

Reference maybe made to U.S. Pat. No. 5,702,491, wherein the hydrogen generation system disclosed comprises a thermally isolated container for containing chemical hydride, a pre-heater to heat the chemical hydride to a predetermined temperature before the chemical hydride is hydrolyzed, a water pipe to supply water into the container to generate hydrogen. The drawback is that this system entails adiabatic arrangement and heating devices, hence results in lower energy efficiency and complicated structure.

Reference may be made to U.S. Pat. No. 5,833,934, discloses a cartridge-type reactor comprising a storage compartment for storing chemical hydride particles, a water absorbent material for retaining water and a water distribution tube for introducing water into the mass of chemical hydride particles. The drawback of the method is relatively low hydrogen content as compared to possible storage in cycloalkanes and irreversible dehydrogenation leading to no-recycling of the hydrides.

Another class of chemical hydrides reported in various prior arts is liquid organic hydride. Liquid organic hydrides such as cycloalkanes are potential hydrogen storage materials due to its high hydrogen content both on volume basis and weight basis. Reference maybe made to U.S. Pat. No. 6,074,447, wherein dehydrogenation of methylcyclohexane, decalin, dicyclohexyl, and cyclohexane to toluene, naphthalene, biphenyl and benzene, respectively, in the presence of particular iridium based molecular complex catalyst at preferably 190° C. or higher is disclosed.

Reference may be made to Japanese Patent JP2001198469, describes hydrogen storage and supply system wherein a catalyst containing at least one metal selected from Ni, Pd, Pt, Rh, Ir, Ru, Mo, Re, W, V, Os, Cr, Co and Fe having good activity for both hydrogenation of hydrogen storage body comprising an aromatic compound and dehydrogenation of a hydrogen supply body comprising the hydrogenated derivative of aromatic compound. The catalysts used are monometallic catalysts which results into relatively lower activity and stability. The metal support interaction is not used for efficient selective dehydrogenation.

Reference may be made to Japanese Patent JP2002134141 describes the equipment used for dehydrogenation of liquid organic hydrides with arrangement for intermittent supply of prescribed amount of liquid organic hydride and a product separator for separating hydrogen from other products.

Reference maybe made to Japanese patents No. JP20001110437 and JP2002134141, wherein use of benzene, toluene, xylene, mesitylene, naphthalene, anthracene, biphenyl, phenanthrene and their alkyl derivatives are possible aromatic substrates used as a means of producing hydrogen for fuel cells has been described. The catalyst used is Pt supported on high surface area substrate.

Chemical hydrides such as $NaBH_4$, $LiBH_4$, $KBH_4$, $RbBH_4$ are reported for storage of hydrogen. Reference maybe made to United States Patent Application 20030014917, wherein a hydrogen generation system comprises: a storage means for storing a chemical hydride solution; a reactor containing a catalyst; a means for supplying the chemical hydride solution from the said storage means to the said reactor so that the chemical hydride solution reacts to generate hydrogen in the presence of the catalyst; and a second supplying means for continuously supplying the solvent of the said solution to the chemical hydride solution during the reaction. The energy system comprises the hydrogen generation system, a fuel cell for generating electricity and water from hydrogen and an oxidant, and a means for recovering the water generated in the said fuel cell and supplying the said water to the chemical hydride solution during the reaction. The chemical hydride hydrogen generation system here uses the solute, which is selected from the group consisting of: $NaBH_4$, $LiBH_4$, $KBH_4$, $RbBH_4$. Generally, chemical hydride reacts with water in the presence of a catalyst to generate hydrogen.

Reference may be made to US Patent Application 20030091876 and US Patent Application 20030091879, wherein the chemical hydride considered are $NaBH_4$, $LiBH_4$, $KBH_4$, $RbBH_4$, $NH_3BH_3$ and combination with water, further include alkaline additives such as LiOH, KOH, NaOH. A chemical hydride hydrogen generation system and an energy system incorporating the same are provided. The hydrogen generation system has: storage means for storing a chemical hydride solution; a reactor containing a catalyst; and a pump for supplying the chemical hydride solution from the storage means to the reactor so that the chemical hydride solution reacts to generate hydrogen in the presence of the catalyst. The hydrogen is supplied to a fuel cell stack. Additionally, a heat transfer circuit is provided including a heat transfer fluid that is circulated through the cooling channels of the fuel cell stack to effect heating thereof on startup, and cooling once the operating temperature is reached.

Reference maybe made to U.S. Patent Application 20030099595, wherein a process for enhancing the kinetics of hydrogenation/dehydrogenation of complex chemical hydrides using mechanomixing and/or mechanomilling is disclosed. The mechano-mixing makes hydrogenation/dehydrogenation of complex chemical hydrides reversible at much reduced temperature and pressure. The mechanomilling claimed to reduce particle size or grain size of the decomposition byproducts, further increasing surface area and intimate contact of the byproducts. In this invention, complex chemical hydride is proposed to be utilized as a reversible hydrogen storage media for various applications such as transportation, including fuel cells. The drawback of the method is mechano-mixing requires long periods and is also energy intensive.

Reference may be made to US Patent Application 20040199039, discloses a method for the gas phase dehydrogenation of hydrocarbons in narrow reaction chambers and integrated reactors. Examples of hydrocarbons for dehydrogenation include propane and isobutane to propylene and isobutene, respectively. Reported in the publication are articles by Jones, et al, and Besser, et al, who describe the gaseous dehydrogenation of cyclohexane in a microreactor. Jones, et al employs a reported feed pressure of 150 kPa and an exit pressure of 1 Pa.

Reference maybe made to U.S. Pat. No. 6,802,875, discloses a hydrogen supply system for a fuel cell which includes a fuel chamber for storing a fuel such as isopropyl alcohol, methanol, benzene, methylcyclohexane, and cyclohexane, a catalytic dehydrogenation reactor, a gas-liquid separation device wherein byproduct is liquefied and separated from the gaseous dehydrogenation reaction product, and a recovery chamber for the hydrogen and dehydrogenated byproduct.

Reference maybe made to US Patent Application No. 20040074759, wherein a process is disclosed for the catalytic reaction of organic compounds, in which the organic compounds are contacted with a catalyst comprising an interstitial metal hydride, having a reaction surface, to produce a catalyst-organic compound mixture. Energy is applied and monatomic hydrogen is produced at the reaction surface of the interstitial metal hydride. The organic compounds are reacted with the monatomic hydrogen. Reactions accomplished by this process include petroleum hydrocracking and hydrotreating processes. The method's performance can be further enhanced using radio frequency (RF) or microwave energy. The drawback of the method is that it requires to produce a catalysts-organic compound mixture thereby poses difficulties in separation of the catalysts and catalysts requirement is generally higher reducing the effective hydrogen storage capacity of the system.

Reference maybe made to U.S. Patent Application 20050002857, wherein processes are provided for the storage and release of hydrogen by means of a substantially reversible catalytic hydrogenation of extended pi-conjugated substrates which include large polycyclic aromatic hydrocarbons, polycyclic aromatic hydrocarbons with nitrogen heteroatoms, polycyclic aromatic hydrocarbons with oxygen heteroatoms, polycyclic aromatic hydrocarbons with alkyl, alkoxy, nitrile, ketone, ether or polyether substituents, pi-conjugated molecules comprising five membered rings, piconjugated molecules comprising six and five membered rings with nitrogen or oxygen hetero atoms, and extended pi-conjugated organic polymers. The hydrogen, contained in the at least partially hydrogenated form of the extended pi-conjugated system, can be released for use by a catalytic dehydrogenation of the latter in the presence of a dehydrogenation catalyst which can be effected by lowering the hydrogen gas pressure, generally to pressures greater than 0.1 bar or raising the temperature to less than 250° C. or less, or by a combination of these two process parameters. The catalysts for hydrogenation is metal selected from group 4, 5, 6 and 8, 9, 10 of the periodic table according to the International Union of Pure and Applied Chemistry. The drawbacks of the method are the process of hydrogenation is carried out at a relative high hydrogen partial pressure and during dehydrogenation its required to maintain partial pressure of hydrogen above 0.1 bar. Also the hydrogen storage capacity obtained was in the range of 1 to 4.7% by weight which is relatively low for economical use of these chemicals. The low hydrogen storage capacity was due to addition of catalyst in reactant itself (particularly 2.3 wt % for pyrene+catalyst and 3.5 wt % for coronene+catalyst) would put weight penalties on transportation. The requirement of means of catalyst separation such as extraction with chloroform is yet another drawback of this system. A high pressure and longer period is required in milling operation. Further in case of some of the pi-conjugated compounds there is irreversible hydrogenation to isomers e.g. in the case of coronene the irreversible hydrogenated product consists of mass 318 isomer upto 20% making the said compound unsuitable for reuse and recycle.

Reference may be made to U.S. Patent no. 20050013767, which discloses a method of delivering a reversible hydrogen storage fuel to a mobile or stationary fuel source. Wherein the patent application describes a fueling process comprising: placing a dispenser comprising a first conduit having an orifice for dispensing a first liquid comprising an at least partially hydrogenated pi-conjugated substrate and a second conduit having an orifice for retrieving a second liquid comprising a pi-conjugated substrate in flow communication with a first compartment and a second compartment; transferring a portion of the first liquid residing in the first compartment into a hydrogen generator and contacting the portion of the stored first liquid with a dehydrogenation catalyst under dehydrogenation conditions sufficient to provide hydrogen and the second liquid; transferring at least a portion of the second liquid into the second compartment; transferring the first liquid through the first conduit into the first compartment and transferring the second liquid through the second conduit. Wherein the pi-conjugated substrate is an extended pi-conjugated substrate selected from the group consisting of extended polycyclic aromatic hydrocarbons, extended piconjugated substrates with nitrogen heteroatoms, extended pi-conjugated substrates with heteroatoms other than nitrogen, pi-conjugated organic polymers and oligomers, ionic pi-conjugated substrates, piconjugated monocyclic substrates with multiple nitrogen heteroatoms, pi-conjugated substrates with at least one triple bonded group, a pitch, and any combination of two or more of the foregoing.

Reference may be made to U.S. Pat. No. 7,101,530, which describes processes provided for the storage and release of hydrogen by means of substantially reversible catalytic hydrogenation of extended pi conjugated substrate which include large polycyclic aromatic hydrocarbons, polycyclic aromatic hydrocarbon with nitrogen heteroatoms, polycyclic aromatic hydrocarbon with oxygen heteroatoms, polycyclic aromatic hydrocarbon with alkyl, alkoxy, ketone, ether or polyether substituent, pi conjugated molecule comprising 5 membered rings, pi conjugated molecule comprising six and five membered rings with nitrogen or oxygen heteroatoms, and extent pi conjugated organic polymers. The hydrogen, contained in the at least partially hydrogenated form of the extended pi conjugated system, can be facilely released for the use by a catalytic dehydrogenation of the latter in presence of dehydrogenation catalyst which can be effected by lowering hydrogen gas pressure, generally to pressure greater than 0.1 bar or raising the temperature less than 250° C. or less, or by a combination of these two process parameters.

Reference may be made to US Patent Application No. 20060143981, which describes an improved process for the storage and delivery of hydrogen by the reversible hydrogenation/dehydrogenation of an organic compound wherein the organic compound is initially in its hydrogenated state. The improvement in the route to generating hydrogen is in the dehydrogenation step and recovery of the dehydrogenated organic compound resides in the following steps: introducing a hydrogenated organic compound to a microchannel reactor incorporating a dehydrogenation catalyst; effecting dehydrogenation of said hydrogenated organic compound under conditions whereby said hydrogenated organic compound is present as a liquid phase; generating a reaction product comprised of a liquid phase dehydrogenated organic compound and gaseous hydrogen; separating the liquid phase dehydrogenated organic compound from gaseous hydrogen; and, recovering the hydrogen and liquid phase dehydrogenated organic compound.

Reference may be made to US Patent Application No. 20100010280 (Catalysts for dehydrogenation of hydrocarbons, 2010) wherein a stationary or fluid bed dehydrogenation catalyst containing an alumina carrier, with chromium and alkali metals consisting of only sodium and potassium, added as promoters is described. The resultant catalyst is demonstrated for dehydrogenation of hydrocarbons.

Reference may be made to P. Taube, M. A. Taube (Liquid organic carrier of $H_2$ as a fuel for automobiles. Adv Hydrogen Energy volume 2, 1981 page no. 1077 to 1082) wherein dehydrogenation of methylcyclohexane was reported for seasonal storage of energy through storage and supply of hydrogen using Pt based catalysts.

Reference maybe made to Journal "R. W. Coughlin, K. Kawakami and A. Hasan (Activity, yield patterns, and coking behavior of Pt and PtRe catalysts during dehydrogenation of methylcyclohexane: I. In the absence of sulfur, Journal of Catalysis Vol. 88, 1984, page numbers 150 to 162) wherein Pt and Pt—Re catalyst has been reported for dehydrogenation of methylcyclohexane to produce hydrogen.

Reference maybe made to Journal "K Jouthimurugesan, S Bhatla, R. D. Srivastava (Kinetics of dehydrogenation of methylcyclohexane over a platinum-rhenium-alumina catalyst in the presence of added hydrogen, Industrial Engineering Chemistry Fundamentals 24(4), 1985 page number 433) wherein kinetics of dehydrogenation of methylcyclohexane over a Pt—Re/alumina catalyst in the presence of added hydrogen has been reported.

Reference may be made to Journal "N. F. Grünenfeldera and Th. H. Schucan (Seasonal storage of hydrogen in liquid organic hydrides: description of the second prototype vehicle, International Journal of Hydrogen Energy, volume 14, issue 8, 1989, page no. 579 to 586)" wherein The MTH-system (methyl cyclohexane, toluene and hydrogen) has been proposed for the seasonal storage of electricity. It consists of two closed loops: in the outer loop hydrogen is produced by electrolysis of water and later burned to give water again. In the inner loop the hydrogen is combined with toluene to give methyl cyclohexane. In this form the energy can be easily stored, transported and finally used throughout the year. At the moment of end use the hydrogen is liberated by splitting the methyl cyclohexane into hydrogen and toluene, and the toluene is recharged with hydrogen later. The most appropriate application of the seasonally stored hydrogen seems to be its use as fuel for heavy vehicles in combustion engines of fuel cells. The exhaust gas of a combustion engine powered by hydrogen consists of water vapour, $N_2$ and NOx. There are no emissions of carbohydrates, carbon monoxide, carbon dioxide or dust particles. The system thus constitutes an important contribution to the protection of the environment. The onboard splitting reaction of methyl cyclohexane to toluene and hydrogen as well as its combination with the hydrogen-fueled combustion engine have been realized and investigated in full scale at our institute. In the present paper we describe the results obtained with the second prototype MTH 2 and we sketch the perspectives for the near future.

Reference may be made to Journal "J. K. Ali, E. J. Newson' and D. W. T. Rippin (Exceeding equilibrium conversion with a catalytic membrane reactor for the dehydrogenation of methylcyclohexane, Chemical Engineering Science. Volume 49, Issue No. 13. Page no. 2129 to 2134, 1994)" where in catalytic membrane reactor containing a tubular palladium-silver (Pd—Ag) membrane sealed in the centre to separate in situ the hydrogen produced, was used to exceed equilibrium limitations in the dehydrogenation of methylcyclohexane. A sulphide, monometallic, noble metal catalyst produced higher than equilibrium yields of toluene and hydrogen from methylcyclohexane at economically viable throughputs. Experiments in the membrane reactor in the temperature range of 573-673 K, pressure. Range of 0.5-2.0 MPa and liquid hourly space velocity range of 2-12 volume feed/h/ reactor volume showed conversions up to 4 times higher than equilibrium values after 300 h onstream and repeated temperature cycling. Exceeding equilibrium was due to the selective permeation of one of the reaction products, i.e. hydrogen, through the membrane. Reactor axial temperature profiles for the reaction with and without a membrane showed that the. total amount of catalyst is more efficiently utilized in the membrane reactor.

Reference may be made to Journal "Scherer, G. W. et al. (International J. hydrogen energy, 1999, 24, 1157)" which disclose the possibility of storing and transporting hydrogen for energy storage via the catalytic gas phase hydrogenation and the gas phase, high temperature, dehydrogenation of common aromatic molecules, e.g., benzene and toluene over Pt/activated carbon catalysts.

Reference may be made to R. O. Loufty and E. M. Vestker in "Investigation of Hydrogen Storage in Liquid organic hydrides" proceedings of the international hydrogen energy forum 2000, Munich Germany, 2000; pages 335-340, wherein they have reported the dehydrogenation of decaline in a membrane reactor where the very low conversion (15%) of decaline, even at 300° C. is greatly enhance by the selective separation of hydrogen by the membrane and its removal from the reactor.

Reference maybe made to Journal "Nobuko Kariya, Atsushi Fukuoka, and Masaru Ichikawa (Efficient evolution of hydrogen from liquid cycloalkanes over Pt-containing catalysts supported on active carbons under "wet-dry multiphase conditions, Applied Catalysis A: General, 233 page 29, 2002)" wherein evolution of hydrogen is reported in the dehydrogenation of cycloalkanes such as cyclohexane, methylcyclohexane, and decalin over Pt catalyst supported on active carbon (AC) under "wet-dry multiphase conditions". Formation rate of hydrogen was largely dependent on reaction conditions such as reactant/catalyst ratio, temperature, and support. The addition of second metals such as Mo, W, Re, Rh, Ir, and Pd on the carbon-supported Pt catalysts reported to result in enhanced dehydrogenation rate due to the promotion of C—H bond cleavage and/or desorption of aromatic products. A physical mixture of Pt/AC and Pd/AC catalysts exhibits higher activities than the monometallic Pt/AC catalyst owing to the synergistic effects of spillover, migration, and recombination of hydrogen over Pt and Pd catalysts.

Reference maybe made to Journal "Shinya Hodoshima, Hiroshi Arai and Yasukazu Saito (Liquid-film-type catalytic decalin dehydrogeno-aromatization for long-term storage and long-distance transportation of hydrogen, International Journal of Hydrogen Energy, Vol. 28, page numbers 197 to 204, 2003)" describing liquid film-type catalytic decalin dehydrogeno-aromatization for long-term storage and long-distance transportation of hydrogen using catalyst Pt/C, Pt—Ir/C and Pt—W/C.

Reference maybe made to Shinya Hodoshima, Hiroshi Arai, Shigeki Takaiwa, Yasukazu Saito (Catalytic decalin dehydrogenation/naphthalene hydrogenation pair as a hydrogen source for fuel-cell vehicle, International Journal of Hydrogen Energy, Vol. 28, page numbers 1255 to 1262, 2003) describing Catalytic decalin dehydrogenation/naphthalene hydrogenation pair as a hydrogen source for fuel-cell vehicle using catalyst Pt/C and Pt—W/C.

Reference maybe made to Journal "Nobuko Kariya, Atsushi Fukuoka, Tadashi Utagawa, Masashi Sakuramoto, Yasushi Goto and Masaru Ichikawa (Efficient hydrogen production using cyclohexane and decalin by pulse-spray mode reactor with Pt catalysts, Applied Catalysis A: General Vol. 247, 2003 page number 247)", wherein highly efficient production of hydrogen without $CO_2$ emission is reported in the dehydrogenation of cyclic hydrocarbons under a non-steady spray pulse operation over supported Pt and Pt-M (M=Re, Rh, Pd) catalysts. Cyclohexane, methylcyclohexane, tetralin and decalin were dehydrogenated by the Pt-containing catalysts supported on thin active carbon cloth sheets and alumite (anodized aluminum) plates. Production rate of hydrogen under the spray pulse mode is reported to be higher than the conventional batch-type liquid phase reaction and the steady state gas phase reaction in the flow system. Production rate of hydrogen was dependent on the rate of reactant feed, the reaction temperature, and the support. Retardation by products adsorbed on the catalysts was negligible under the spray-pulse operation.

Reference maybe made to Journal "Rajesh B. Biniwale, Nobuko Kariya, and Masaru Ichikawa (Dehydrogenation of Cyclohexane Over Ni Based Catalysts Supported on Activated Carbon using Spray-pulsed Reactor and Enhancement in Activity by Addition of a Small Amount of Pt, Catalysis Letters Vol. 105, Nos. 1-2, November, 2005 page numbers 83 to 87)", wherein dehydrogenation of cyclohexane over Ni based catalysts supported on activated carbon using spray-pulsed reactor and enhancement in activity by addition of a small amount of Pt is reported for hydrogen storage and supply application.

Reference maybe made to Journal "Shinya Hodoshima, Shigeki Takaiwa, Atsushi Shono, Kazumi Satoh and Yasukazu Saito (Hydrogen storage by decalin/naphthalene pair and hydrogen supply to fuel cells by use of superheated liquid-film-type catalysis, Applied Catalysis A: General Vol. 283, 2005 page numbers 235 to 242)" wherein hydrogen storage by decalin/naphthalene pair and hydrogen supply to fuel cells by use of superheated liquid-film-type catalysis and Pt/C catalysts is described.

Reference maybe made to Journal "Shinya Hodoshima, Hiroaki Nagata and Yasukazu Saito (Efficient hydrogen supply from tetralin with superheated liquid-film-type catalysis for operating fuel cells, Applied Catalysis A: General Vol. 292, 2005 page numbers 90 to 96)" reports efficient hydrogen supply from tetralin with superheated liquid-film-type catalysis and using catalysts namely Ni/C, Ru/C and Ni—Ru for operating fuel cells.

Reference maybe made to Journal "Yoshimi Okada, Eiji Sasaki, Eiji Watanabe, Shinji Hyodo and Hiroaki Nishijima (Development of dehydrogenation catalyst for hydrogen generation in organic chemical hydride method, International Journal of Hydrogen Energy, Vol. 31, 2006 page numbers 1348 to 1356) wherein dehydrogenation of methylcyclohexane has been reported on K—Pt/Al$_2$O$_3$ catalyst when heated near to 320° C.

Reference may be made to Journal "Sevim Yolcular, Ozden Olgun (Ni/Al2O3 catalysts and their activity in dehydrogenation of methylcyclohexane for hydrogen production, Catalysis Today volume 138, 2008, page no. 198 to 202)" wherein dehydrogenation of methylcyclohexane has been reported over Ni/Al$_2$O$_3$ catalysts in the temperature range of 653-713 K.

Reference may be made to Journal "Yasukazu Saitoa, Kiyoshi Aramakia, Shinya Hodoshima, Morihiro Saito, Atsushi Shono, Jun Kuwanoa and Katsuto Otake (Efficient hydrogen generation from organic chemical hydrides by using catalytic reactor on the basis of superheated liquid-film concept, Chemical Engineering Science volume 63 issue 20, 2008 page no. 4935 to 4941)" wherein under boiling and refluxing conditions for catalytic dehydrogenation of organic chemical hydrides (decalin, methylcyclohexane and others) in a batch-wise reactor, either suspended states with excess amounts of substrate or sand-bath states with its scarce amounts were found to be inferior generally to the so-called "liquid-film states" with adequate amount ratios of substrate to catalyst, where the catalyst-layer temperatures were superheated or raised higher than the boiling point, and, consequently, reactivities became more favorable at higher heating temperatures in contrast to the boiling suspended states. Equilibrium shifts due to reactive distillation were well demonstrated under boiling and refluxing conditions in naphthalene dehydrogenation. Moreover, desorption of hydrogen from the active sites to the bubble space was enhanced in the superheated liquid-film states, with large translational entropy endowed.

Reference may be made to Journal "Rajesh B. Biniwale, S. Rayalu, S. Devotta, M. Ichikawa (Chemical hydrides: A solution to high capacity hydrogen storage and supply, International Journal of Hydrogen Energy, Volume 33, Issue 1, January 2008, Pages 360-365)" wherein a review of various catalysts for dehydrogenation of cycloalkanes is reported. The catalysts include Pt, Ni supported on either activated carbon or alumite.

Reference may be made to Journal "Anshu Shukla, Priti Gosavi, Jayhshri Pande, Vanama Kumar, K. V. R. Chary, Rajesh Biniwale (Efficient hydrogen supply through catalytic dehydrogenation of methylcycklohexane over Pt/metal oxide catalyst, International journal of hydrogen energy, volume 35, 2010, page no. 4020-4026)" wherein catalysts consisting of Pt supported on various metal oxide including La$_2$O$_3$, Al$_2$O$_3$, TiO$_2$, ZrO$_2$, CeO$_2$, MnO$_2$, Fe$_2$O$_3$ has been reported. A further Pt/LaNiO$_3$ and Pt/La$_{0.7}$Y$_{0.3}$NiO$_3$ catalyst has been reported for dehydrogenation of methylcyclohexane. However the activity of catalysts is relatively lower.

The literature available on the hydrogen storage and supply indicated the use of dehydrogenation of hydrogenated organic hydrocarbons for carrying hydrogen. Several other chemical hydrides are also reported. The literature appears to use the noble metal, particularly Pt as catalyst along with a few bimetallic catalysts such as Ni—Pt. Use of bimetallic catalysts for spillover, migration and recombination of abstracted H atoms for purpose of dehydrogenation of hydrogenated liquid organic compound is barely reported. The stability of catalyst in prior art is relatively lower. Further, in case of monometallic catalyst the selectivity towards dehydrogenation is lower.

OBJECTIVES OF THE INVENTION

The main object of the present invention is to provide improved process for delivery of hydrogen through dehydrogenation of hydrogenated liquid organic compounds through dehydrogenation reaction over catalysts with general formula M/support and M-M'/support where M and M' are metals which obviates the drawbacks of the hitherto known prior art as detailed above.

Another objective of the present invention is to provide to use of pure hydrogen for hydrogen storage, transportation and delivery using hydrogenated liquid organic compounds for utilization in fuel cell applications including mobile and stationary application and any other application wherein pure hydrogen is required. The other applications may include hydrogen supply to vegetable oil industry, glass industry etc.

Another objective of the present invention is to provide hydrogen supply system consist of hydrogenated organic compounds in liquid form containing hydrogen in chemically bonded form, includes cyclohexane, methylcyclohexane, decalin or liquid pi conjugated form of organic compound.

Yet another object of the present invention is to provide catalysts with general formula M-M'/support where M is at least one metal selected from group 11 of periodic table metals Cu, Ag, Au and M' is at least one metal selected from Pt, Pd, Rh, Ru, Ir, Os, Fe, Ni, Re, Mo, W, V, Cr, Co or combinations thereof well dispersed on high surface area supports such as activated carbon, alumina, alumite, zirconia, silica or combination thereof.

Yet another objective of this invention is to provide catalysts with general formula M/support where M is at least one metal selected from Pt, Pd, Rh, Ru, Ir, Os and support is metal oxides at least one selected from $Y_2O_3$, $V_2O_5$ or combinations thereof.

Yet another objective of the present invention is to provide well dispersed metal catalyst and to employ it in minimum diffusion area reactor such as micro reactor for efficient heat transfer to catalyst for carrying out endothermic dehydrogenation reaction efficiently.

Yet another object of the present invention is to provide a means for hydrogen delivery with hydrogen storage on high weight and volume basis and transported at near ambient temperature and pressure conditions in the form of hydrogenated liquid organic compounds.

Yet another object of the present invention is to provide a means for delivery of clean hydrogen free from any contaminant for fuel cell applications.

Yet another object of the present invention is to provide a means for carrying out catalytic dehydrogenation of hydrogenated liquid organic compounds in the temperature range of 120 to 400° C. and in the pressure range of 1.2 to 10 bars.

Yet another object of the present invention is to provide a hydrogen storage media with 2-8 weight percent hydrogen capacity and on volume basis 10-65 kg of hydrogen per $m^3$ of volume.

Yet another object of the present invention is to provide a means for hydrogen delivery to remote refueling stations or hydrogen based power generators by using simple structures such as lorries.

Yet another object of the present invention is to provide a means for hydrogen delivery to industrial applications such as vegetable oil industry, glass industry etc.

SUMMARY OF THE INVENTION

Accordingly, present invention provides an improved process for the delivery of hydrogen comprises dehydrogenating hydrogenated liquid organic compounds using catalyst in dehydrogenation reactor, the catalyst being heated at temperature in the range of 120-400° C. followed by separating the hydrogen evolved by cooling to temperature in the range of 2-50° C. to obtain hydrogen free from any contaminant where in catalyst are selected from:
  i. M/support wherein metal M is at least one metal selected from the group consisting of Pt, Pd, Rh, Ru, Ir, Os and said metal being dispersed on support which is a metal oxide at least one selected from $Y_2O_3$ or $V_2O_5$ or combinations thereof or;
  ii. M-M'/support wherein metal M is at least one metal selected from Cu, Ag, Au, metal M' is at least one metal selected from Pt, Pd, Rh, Ru, Ir, Os, Fe, Ni, Re, Mo, W, V, Cr, Co or combinations thereof and said metal being dispersed on support which is selected from the group consisting of activated carbon, alumina, alumite, zirconia, silica or combination thereof.

In an embodiment of the present invention, wherein quantity of M varied from 2 to 20 wt % of the support weight in M/Support type metal catalyst and quantity of M varied from 2 to 20 wt % of the support weight and M' varied from 0.1 to 3 wt % of the support weight in M-M'/support type metal catalyst.

In another embodiment of the present invention, hydrogenated liquid organic compounds is selected from compounds containing hydrogen in chemically bonded form, capable of storing hydrogen of 2-8 weight percent and 10-62 kg of hydrogen per m3 of volume.

In the present invention, the hydrogenated liquid organic compounds are selected from the group consisting of cyclohexane, methyl cyclohexane, decalin, 2-propanol or liquid Pi conjugated form of organic compounds.

In yet another embodiment of the present invention, catalyst is heated by at least one of the sources selected from electrical heater, thermic fluid or renewable energy resources or combination thereof.

In yet another embodiment of the present invention, the preferable resource is renewable energy resources such as solar concentrator.

In yet another embodiment of the present invention, catalyst used is in the nanostructured with sizes varying from 3 to 100 nm.

In yet another embodiment of the present invention, dehydrogenation reactor used is selected from microchannel reactor, pulse-spray reactor, continuous reactor, column reactor of cross section of rectangular, triangular, elliptical, circular or any irregular shape.

In yet another embodiment of the present invention, hydrogen evolution rate using M/support is in the range of 300 to 1000 mmol/$g_{met}$/min and using M-M'/support is in the range of 10 to 70 mmol/$g_{met}$/min.

In yet another embodiment of the present invention, conversion efficiency of organic compound and hydrogen storage capacity is in the range of 20 to 99% and 1.44 to 6.1 wt % respectively.

In yet another embodiment of the present invention, hydrogen generated is supplied to applications including fuel cells in mobile applications, fuel cells in stationary applications, vegetable oil industry or glass industry.

In an embodiment of the present invention the catalyst is placed in a reactor with minimum diffusion area or creating alternate dry-wet conditions and the catalyst is heated to temperature of 120-400° C. using thermal, electrical means or preferably by renewable energy sources such as a solar concentrator the product of the reaction are separated by cooling to temperature range of 2-50° C., hydrogen obtained is thus free from any contaminant and useful for fuel cell applications, hydrogen is fed as carrier gas to the reactor to maintain purity of hydrogen in the outlet product from the reactor.

In another embodiment of the present invention, the dehydrogenation reaction is carried in a spray-pulsed injection mode by varying injection frequency of reactant feed from 0.1 to 1 Hz.

In yet another embodiment of the present invention, the dehydrogenation reaction is carried in a spray-pulsed injection mode by varying pulse width of reactant feed from 1 to 10 ms.

In yet another embodiment of the present invention, the dehydrogenation reaction is carried in a micro channel reactor.

In still another embodiment of the present invention, the dehydrogenation catalysts is Ag/activated carbon prepared by wet chemistry method with preferred quantity of Ag from about 2 to 20 wt % based on the weight of the support.

In yet another embodiment of the present invention, the dehydrogenation catalysts is Ag—Pt/activated carbon prepared by wet chemistry method wherein preferred quantity of Ag is in the range of 2 to 20 wt % and preferred quantity of Pt is in the range of 0.1 to 3 wt % based on the weight of the catalyst support.

In yet another embodiment of the present invention, the dehydrogenation catalysts is Ag—Pd/activated carbon prepared by wet chemistry method wherein preferred quantity of Ag is in the range of 2 to 20 wt % and Pd loading is in the range of 0.1 to 3 wt % based on the weight of the support.

In yet another embodiment of the present invention, the dehydrogenation catalysts is Ag—Rh/activated carbon prepared by wet chemistry method wherein preferred quantity of Ag is in the range of 2 to 20 wt % and preferred quantity of Rh is in the range of 0.1 to 3 wt % based on the weight of the support.

In yet another embodiment of the present invention the dehydrogenation catalysts is Ag—Ru/activated carbon prepared by wet chemistry method wherein preferred quantity of Ag is in the range of 2 to 20 wt % and preferred quantity of Ru is in the range of 0.1 to 3 wt % based on the weight of the support.

In yet another embodiment of the present invention, the dehydrogenation catalysts is Pt/$V_2O_5$ prepared by wet chemistry method wherein preferred quantity of Pt is in the range of 2 to 20 wt % based on the weight of the support.

In still another embodiment of the present invention, the dehydrogenation catalysts are heated by electrical heater or by using a solar concentrator.

In yet another embodiment of the present invention, a swip gas either $N_2$ or $H_2$, preferably $H_2$ is employed to transfer produced hydrogen to outlet of the reactor.

In yet another embodiment of the present invention, the gas from after cleaning is monitored for its quality and quantity by using analytical techniques such as gas chromatograph.

In yet another embodiment of the present invention, hydrogen is fed as carrier gas to the reactor to maintain purity of hydrogen in the outlet product from the reactor.

DETAILED DESCRIPTION OF THE INVENTION

Present invention provides catalysts for dehydrogenation of hydrogenated liquid organic compounds for hydrogen storage and supply which comprises Metal catalysts with general formula M/support and M-M'/support which can be used for releasing hydrogen from hydrogenated liquid organic compounds through dehydrogenation reaction.

There are two different types of catalysts are used in this invention as following;
1) In the first type of catalysts M-M'/support, metal M is at least one metal selected from group 11 of periodic table metals Cu, Ag, Au and metal M' is at least one metal selected from Pt, Pd, Rh, Ru, Ir, Os, Fe, Ni, Re, Mo, W, V, Cr, Co or combinations thereof well dispersed on high surface area supports such as activated carbon, alumina, alumite, zirconia, silica or combination thereof. The addition of second metal selected from Pt, Pd, Rh, Ru, Ir, Os, Fe, Ni, Re, Mo, W, V, Cr, Co and at least one metal selected from group 11 metals such as Cu, Ag and Au exhibits the synergistic effects of spillover, migration, and recombination of hydrogen over metallic catalysts having minimum of two metals resulting in shifting of equilibrium to dehydrogenation reaction.
2) In the second type of catalyst M/support, noble metal catalysts dispersed on metal oxide supports wherein M is at least one metal selected from Pt, Pd, Rh, Ru, Ir, Os and support is metal oxide at least one selected from $Y_2O_3$, $V_2O_5$, or combinations thereof.

The catalyst M-M'/support is designed in such a way that the quantity of metal M is 2 to 20 wt % of the support weight and quantity of metal M' is 0.1 to 3 wt % of support weight.

The catalyst M/support is designed in such a way that the quantity of metal M varied from 2 to 20 wt % of the support.

The catalysts in this invention are useful for dehydrogenation of hydrogenated liquid organic compound selected from cyclohexane, methyl cylcohexane, decalin, 2-propanol and liquid Pi conjugated form of the organic compounds.

Figure 1:
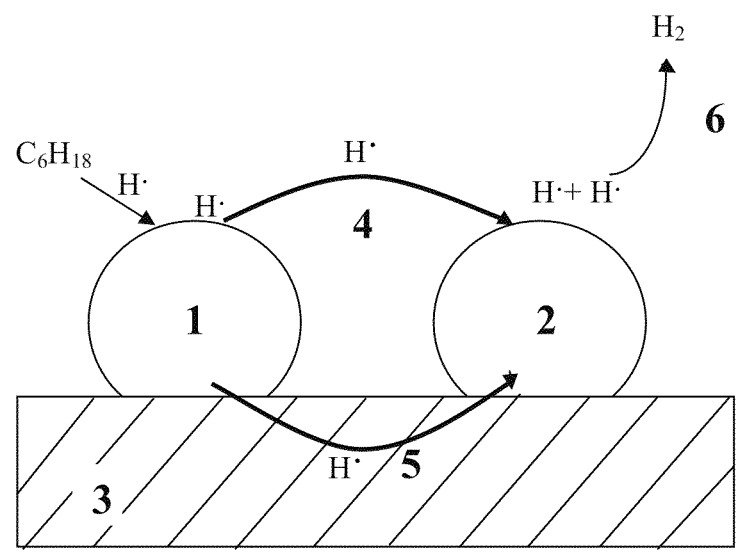
FIG. 1 is schematic of mechanism of dehydrogenation over at least two different metals existing over support.

In the case of M-M'/support catalysts the use of more than one metal selected from Pt, Pd, Rh, Ru, Ir, Os, Fe, Ni, Re, Mo, W, V, Cr, Co in combination with at least one metal selected from group 11 metals Cu, Ag, Au or combinations thereof as catalyst in the present invention is expected to exhibit the synergistic effects of spillover, migration, and recombination of hydrogen over metallic catalysts having minimum of two metals resulting in shifting of equilibrium to dehydrogenation reaction. Therefore the activity and selectivity of the catalysts is improved. The phenomenon can be explained as depicted in FIG. 1. Two metal M [1] and M' [2] dispersed on support [3] facilitates the reaction. The reactant (for example cyclohexane is shown in this figure, but not limited to) adsorb on any metal [1] and abstraction of H atom takes place. The H atom spillover [4] or migrate [5] through support [3] on second metal [2] and recombine [6] to form molecular hydrogen.

In metal oxides hydrogen spillover is favorable because of the thermodynamic and small energy barrier. This can be attributed to easy migration of H atom from catalyst to substrate and subsequent proton diffusion in the bulk. Therefore, using metal oxide as support is expected to result into better hydrogen spillover and in turn better catalytic activity for dehydrogenation. This provides the second metal along with Pt on the catalyst surface as active sites for hydrogen abstraction, spillover and recombination. The use of metal oxide as support under the reducing condition is expected to result into migration of active metal species from metal oxides to the surface thereby providing additional active sites. Therefore catalyst in the present invention is expected to exhibit the synergistic effects of spillover, migration, and recombination of hydrogen over noble metal catalysts having two metals under reducing conditions resulting in shifting of equilibrium to dehydrogenation reaction.

Figure 2:
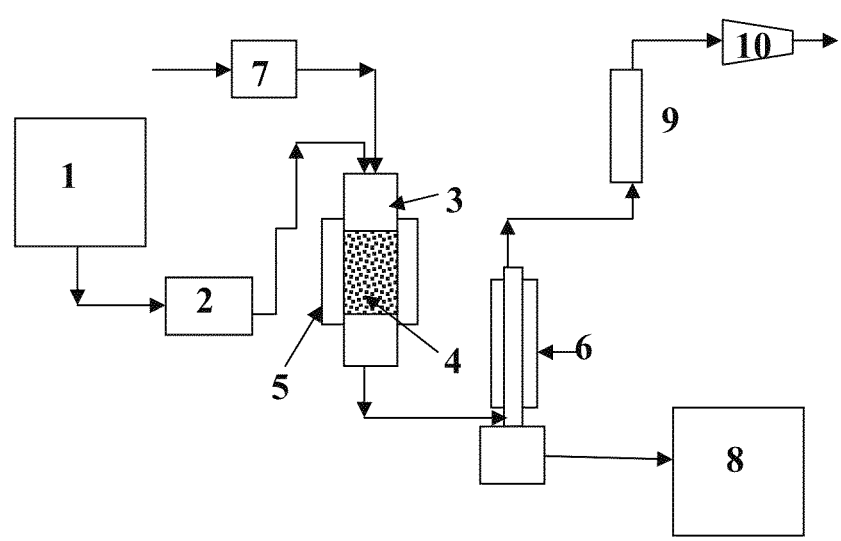
FIG. 2 is schematic of system for dehydrogenation of hydrogenated organic compounds.

The dehydrogenation catalyst of the present invention can be utilized in either a fixed bed reactor, spray pulsed reactor or micro channel reactor. In case of fixed bed reactor as Shown in FIG. 2 the dehydrogenation system consists of storage for hydrogenated liquid organic compound [1], which is fed through a flow pump and controller [2] to the reactor [3] with circular or square or rectangular or any other cross section. In reactor [3] a dehydrogenation catalysts [4] either with general formula M/support or M-M'/support is kept and heated with heating arrangement [5]. The heating is provided by using electrical heater or thermic fluid coil or more preferably renewable energy source such as solar concentrators. The catalysts temperature is maintained in the range of 120 to 400° C. The products are separated by using a suitable device such as a condenser [6]. A carrier gas is also introduced in the reactor through a flow meter [7]. The liquid part from the separated product is stored in storage [8] and gaseous product i.e. hydrogen is passed through an entrainment separator [9] to clean the hydrogen. The hydrogen gas is then passed to compressor [10] for supply to the various applications.

Figure 3:
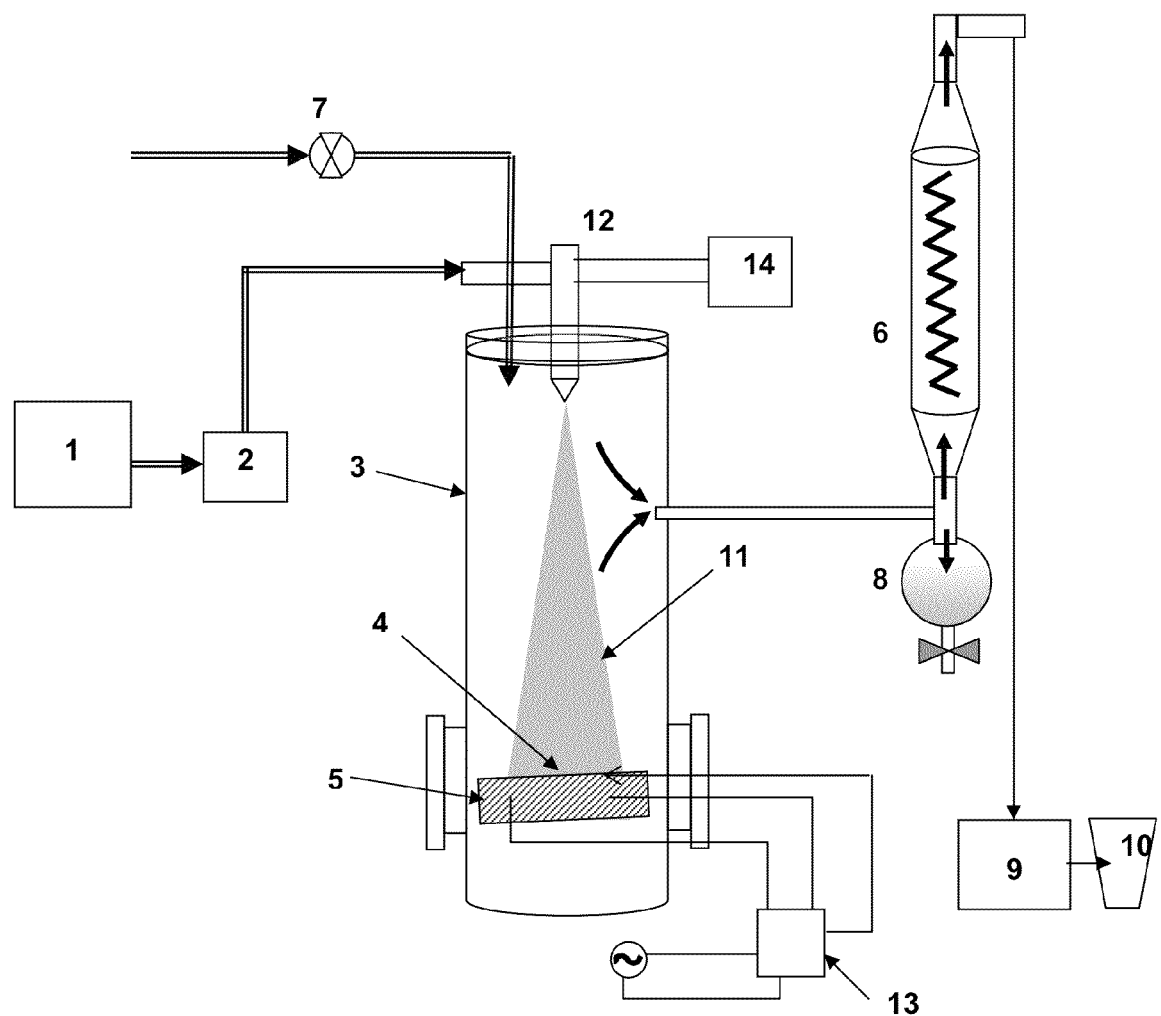
FIG. 3 is a schematic of system for dehydrogenation of hydrogenated organic compounds wherein the reactor is a pulsed spray type of reactor.

In a particular reaction setup using spray pulse reactor as depicted in FIG. 3, the dehydrogenation system consists of storage for hydrogenated liquid organic compound [1], which is fed through a flow pump and controller [2] to the reactor [3]. The reactor [3] is having spray-pulsed mechanism for injection of reactant. The catalyst [4] is placed in the reactor in such a way that the reactant feed [11] in atomized form is sprayed using one or more fine nozzles [12] over the catalysts. The catalyst [4] is heated by using heater arrangement [5] and temperature is controlled by a temperature controller [13]. The pulse injection frequency and pulse width is controlled by frequency generator [14]. The catalysts temperature is maintained in the range of 120 to 400° C. The products are separated by using a suitable device such as a condenser [6]. A carrier gas is also introduced in the reactor through a flow meter [7]. The liquid part from the separated product is stored in storage [8] and gaseous product i.e. hydrogen is passed through an entrainment separator [9] to clean the hydrogen. The hydrogen gas is then passed to compressor [10] for supply to the various applications.

The performance of catalysts was evaluated by monitoring the gaseous products from reactor using gas chromatography equipped with thermal conductivity detector. The condensate consisting aromatics and unreacted reactant was analysed on gas chromatograph with flame ionisation detector.

Since the hydrogen generated is without any contamination the system is useful for supply of hydrogen for applications such as fuel cell, vegetable oil industry, glass industry etc. Corresponding aromatics formed is condensed and recycled for subsequent hydrogenation to carry more hydrogen. The metal catalyst is kept in reduced state by hydrogen produced during reaction.

The system in the present invention is for establishing stand-alone hydrogen fuelling station based on renewable energy. Therefore, the advantages expected to be achieved by the use of the catalytic materials according to the present invention are novel.

Present invention provides efficient catalysts having conversion efficiencies in the range of 30-98% for dehydrogenation of hydrogenated liquid organic compounds. The effective hydrogen storage capacity of 2-8 wt % can be obtained. Further, on volume basis 10-62 Kg of hydrogen per $m^3$ of volume can be stored.

The steps involve in the present invention are:

Design and synthesis of a catalysts with general formula M/support and M-M'/support, wherein case of M/support M is at least one metal selected from Pt, Pd, Rh, Ru, Ir, Os and support is metal oxide at least one selected from $Y_2O_3$ or $V_2O_5$ or combinations thereof.

In the second type of catalysts M-M'/support, metal M is at least one metal selected from group 11 of periodic table metals Cu, Ag, Au and metal M' is at least one metal selected from Pt, Pd, Rh, Ru, Ir, Os, Fe, Ni, Re, Mo, W, V, Cr, Co or combinations thereof well dispersed on high surface area supports such as activated carbon, alumina, alumite, zirconia, silica or combination thereof. The addition of second metal selected from Pt, Pd, Rh, Ru, Ir, Os, Fe, Ni, Re, Mo, W, V, Cr, Co and at least one metal selected from group 11 metals such as Cu, Ag and Au exhibits the synergistic effects of spillover, migration, and recombination of hydrogen over metallic catalysts having minimum of two metals resulting in shifting of equilibrium to dehydrogenation reaction.

Use of strong metal/support interaction to promote better hydrogen dispersion of metal catalyst and hydrogen spillover due to properties of support facilitating migration of H atoms from active metal site to support after abstraction of H atoms from cycloalkanes on the metal site. This avoids the reverse reaction and thus favours better catalytic activity.

In case of M-M'/support catalysts addition of second metal in such a way to have close interaction between two metal for possible hydrogen spillover, migration and recombination to improve catalyst activity.

Use of suitable method for loading of metal catalysts on support namely wet impregnation or adsorption or polyol method. Polyol method is used for metal cluster formation or synthesis methods for bimetallic catalyst. Wherein metal salts (particularly metal nitrates) are dissolved in ethylene glycol (0.1 g of metal equivalent in 10 ml of ethylene glycol), poly vinyl pyrolidone (PVP with molecular weight of ca 40000) is added in a quantity equal to 0.1% of the weight of metal. The mixture has been treated in microwave for 1 to 5 minutes.

Using the catalyst in present invention in suitable reactions such as packed bed, spray pulse or micro channel reactor for carrying out dehydrogenation of hydrogenated liquid organic compounds in the temperature range of 120-400° C.

Using renewable energy for catalyst heating by employing solar concentrator.

EXAMPLES

The following examples are given by way of illustration of the working of the invention in actual practice and therefore should not be construed to limit the scope of the present invention.

Examples of Bimetallic Catalysts Supported on Activated Carbon Cloth

Example 1

A bimetallic catalyst was synthesized by adsorption method using activated carbon cloth as support and $AgNO_3$ and $H_2PtCl_6$ as metal precursor with 10 wt % of Ag loading and 1 wt % of Pt in final product. $AgNO_3$ salt was dissolved in 20 ml acetone to prepare 0.025M solution. Carbon cloth was separately cleaned by boiling it in acetone at about 80° C. and dried in oven at 60° C. for 30 min. Then $AgNO_3$ salt solution was added to the cleaned carbon cloth and was allowed to shake for 12 hrs using a mechanical shaker at 27° C. The above sample was then decanted and dried at 80° C. for 6 hrs. Platinum loading was achieved by wet impregnation method. $H_2PtCl_6$ salt was dissolved in acetone of about 20 ml to prepare 0.02 M solution and was added to the host catalyst followed by drying at 60° C. The catalyst thus prepared was designated as Ag10 Pt1/Carbon Cloth.

Example 2

The catalyst as described in the example 1, 10 wt % Ag-1 wt % Pt/CC was used for carrying out dehydrogenation of cyclohexane using a specially designed spray-pulsed reactor. A cylindrical reactor was used with an injection nozzle at the top of the reactor. The catalysts were placed at the center of the reactor with arrangement for heating and a temperature controller. The nozzle was placed in such a way to inject atomized spray of reactant over catalysts. The reactant was sprayed in a periodic manner after every 1 sec. The injection frequency and injection pulse with in terms of 0.3 Hz and 10 ms respectively by a frequency regulator. The reaction was carried out in nitrogen atmosphere at pressure of 1.2 atm. The hydrogen generated was monitored using gas chromatograph for product gas analysis. The conversion efficiency for cyclohexane over 10 wt % Ag-1 wt % Pt/CC catalyst at 300° C. was 65% resulting into hydrogen storage capacity of 4.68 wt % and 40.3 kg/m³ on volume basis was obtained.

Example 3

Bimetallic catalyst was synthesized by using activated carbon cloth as support and $AgNO_3$ and $RhCl_3$ as metal precursor with 10 wt % of Ag loading and 1 wt %) of Rh in final product. $AgNO_3$ salt was dissolved in about 20 ml acetone to prepare 0.02M solution. Carbon cloth was separately cleaned by boiling it in acetone at about 80° C. and dried in oven at 60° C. for 30 min. Then $AgNO_3$ salt solution was added to the cleaned carbon cloth and was allowed to shake for 12 hrs using a mechanical shaker at 30° C. The above sample was then decanted and dried at 80° C. for 6 hrs. Rhodium loading was achieved by wet impregnation method. $RhCl_3$ salt 0.047 M was dissolved in acetone of about 20 ml and was added to the host catalyst followed by drying at 60° C. The catalyst thus prepared was designated as Ag10Rh1/CC.

Example 4

The catalyst as described in the example 3, 10 wt % Ag-1 wt % Rh/CC was used for carrying out dehydrogenation of cyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner of 1 sec. The injection frequency and injection pulse with in terms of 0.3 Hz and 10 ms respectively by a frequency regulator. The reaction was carried out in nitrogen atmosphere at a pressure of about 1.2 atm. The hydrogen generated was monitored using gas chromatograph for product gas analysis. The conversion efficiency for cyclohexane over 10 wt % Ag-1 wt % Rh/CC catalyst at 300° C. was 60% resulting into 4.32 wt % of hydrogen storage and 37.2 kg/m³ on volume basis was obtained.

TABLE 1

Comparative table for various catalysts exhibits hydrogen evaluation rate under same conditions and at temperature of 300° C. during dehydrogenation of cyclohexane

| Sr. No. | Catalyst | Hydrogen evolution rate (mmols/$g_{met}$/min) | Average size of the catalysts particle (nm) |
|---|---|---|---|
| 1 | 10 Ag—1Rh/C | 12.34 | 10 |
| 2 | 10Ag—1 Pt/C | 13.36 | 7 |
| 3 | AgP/C | 1.99 | 20 |
| 4 | Ag—RhP/C | 46.11 | 10 |
| 5 | Ag—PtP/C | 56.98 | 6 |
| 6 | Ag—PdP/C | 61.85 | 9 |

Examples of Monometallic and Bimetallic Catalysts Prepared by Polyol Method Supported on Activated Carbon Cloth

Example 5

Monometallic catalyst was synthesized by using activated carbon cloth as support and $AgNO_3$ as metal precursor with 10 wt % as final loading. Ag Nanoparticles was synthesized by microwave polyol method. $AgNO_3$ salt was dissolved in 20 ml ethylene glycol to prepare 0.1 M solution and 0.02 g of PVP was added. The beaker was placed in the center of the domestic Microwave oven and heated for 60 s. The catalyst was synthesized by incipient wet method. Carbon cloth was separately cleaned by boiling it in acetone at about 80° C. and then dried in oven at 60° C. for 30 min. The cleaned carbon cloth was impregnated by an appropriate amount of solution containing metal equivalent to targeted loading of 10 wt % over activated cloth. The catalyst thus prepared was designated as AgP1/CC.

Example 6

The catalyst as described in the example 7, 10 wt % AgPt1/CC was used for carrying out dehydrogenation of cyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner of 1 sec. The injection frequency and injection pulse with in terms of 0.3 Hz and 10 ms respectively by a frequency regulator. The reaction was carried out in nitrogen atmosphere at a pressure of about 1.2 atm. The hydrogen generated was monitored using gas chromatograph for product gas analysis. The conversion efficiency for cyclohexane over 10 wt % AgP1/CC catalyst at 300° C. was 20% resulting into 1.44 wt % of hydrogen storage and 12.4 kg/m³ on volume basis was obtained.

Example 7

Bimetallic catalyst was synthesized by using activated carbon cloth as support and $AgNO_3$ and $H_2PtCl_6$ as metal precursor with 5 wt % of Ag and 5 wt % of Pt as final loading. Ag—Pt Nanoparticles was synthesized by microwave polyol method. $AgNO_3$ salt was dissolved in 20 ml ethylene glycol to prepare 0.1 M solution and 0.02 g of PVP was added, the beaker was placed in the center of the domestic Microwave oven and heated for 60 s. $H_2PtCl_6$ salt was dissolve in 20 ml ethylene glycol and added to Ag solution and again microwave for 60 s. The catalyst was synthesized by incipient wet method. Carbon cloth was separately cleaned by boiling it in acetone at about 80° C. and then dried in oven at 60° C. for 30 min. The cleaned carbon cloth was impregnated by an appropriate amount of solution containing metal equivalent to targeted loading of 10 wt % over activated cloth where in the calculated wt % ratio was 1:1 The catalyst thus prepared was designated as AgPtP/CC.

Example 8

The catalyst as described in the example 9, AgPtP/CC was used for carrying out dehydrogenation of cyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner of 1 sec. The injection frequency and injection pulse with in terms of 0.3 Hz and 10 ms respectively by a frequency regulator. The reaction was carried out in nitrogen atmosphere at a pressure of about 1.2 atm. The hydrogen generated was monitored using gas chromatograph for product gas analysis. The conversion efficiency for cyclohexane over 10 wt % AgPtP/

CC catalyst at 300° C. was 70% resulting into 5.04 wt of hydrogen storage and 43.4 kg/m³ on volume basis was obtained.

Example 9

Bimetallic catalyst was synthesized by using activated carbon cloth as support and $AgNO_3$ and $PdCl_2$ as metal precursor with 5 wt % of Ag and 5 wt % of Pd as final loading. Ag—Pd Nanoparticles was synthesized by microwave polyol method. $AgNO_3$ salt was dissolved in 20 ml ethylene glycol to prepare 0.1 M solution and 0.02 g of PVP was added. The beaker was placed in the center of the domestic Microwave oven and heated for 60 s. $PdCl_2$ salt was dissolve in 20 ml ethylene glycol and added to Ag solution and again microwave for 60 s. The catalyst was synthesized by incipient wet method. Carbon cloth was separately cleaned by boiling it in acetone at about 80° C. and then dried in oven at 60° C. for 30 min. The cleaned carbon cloth was impregnated by an appropriate amount of solution containing metal equivalent to targeted loading of 10 wt % over activated cloth where in the calculated wt % ratio was 1:1 The catalyst thus prepared was designated as AgPdP/CC.

Example 10

The catalyst as described in the example 11, AgPdP/CC was used for carrying out dehydrogenation of cyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner of 1 sec. The injection frequency and injection pulse with in terms of 0.3 Hz and 10 ms respectively by a frequency regulator. The reaction was carried out in nitrogen atmosphere at a pressure of about 1.2 atm. The hydrogen generated was monitored using gas chromatograph for product gas analysis. The conversion efficiency for cyclohexane over 10 wt % AgPdP/CC catalyst at 300° C. was 70% resulting into 5.04 wt % of hydrogen storage and 43.4 kg/m³ on volume basis was obtained.

Example 11

Bimetallic catalyst was synthesized by using activated carbon cloth as support and $AgNO_3$ and $RhCl_3$ as metal precursor with 5 wt % of Ag and 5 wt % of Rh as final loading. Ag—Rh Nanoparticles was synthesized by microwave polyol method. $AgNO_3$ salt was dissolved in 20 ml ethylene glycol to prepare 0.1 M solution and 0.02 g of PVP was added. The beaker was placed in the center of the domestic Microwave oven and heated for 60 s. $RhCl_3$ salt was dissolve in 20 ml ethylene glycol and added to Ag solution and again microwave for 60 s. The catalyst was synthesized by incipient wet method. Carbon cloth was separately cleaned by boiling it in acetone at about 80° C. and then dried in oven at 60° C. for 30 min. The cleaned carbon cloth was impregnated by an appropriate amount of solution containing metal equivalent to targeted loading of 10 wt % over activated cloth where in the calculated wt % ratio was 1:1 The catalyst thus prepared was designated as AgRhP/CC.

Example 12

The catalyst as described in the example 13, AgRhP/CC was used for carrying out dehydrogenation of cyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner of 1 sec. The injection frequency and injection pulse with in terms of 0.3 Hz and 10 ms respectively by a frequency regulator. The reaction was carried out in nitrogen atmosphere at a pressure of about 1.2 atm. The hydrogen generated was monitored using gas chromatograph for product gas analysis. The conversion efficiency for cyclohexane over 10 wt % AgRhP/Carbon Cloth catalyst at 300° C. was 55% resulting into 3.96 wt % of hydrogen storage and 34.1 kg/m³ on volume basis was obtained.

Examples Related to Noble Metal Catalyst Supported on Metal Oxides

Example 13

A catalyst was synthesized by using $Y_2O_3$ as support and $PtCl_4$ as metal precursor with 3 wt % of Pt loading in final product. $Y_2O_3$ was dried in oven at 80° C. for 2 h. Platinum loading over $Y_2O_3$ was achieved by wet impregnation method, wherein $PtCl_4$ was taken as 21.11 ml with the molar concentration of 0.02 M. The prepared catalyst was dried in oven at 100° C. The catalyst thus prepared was designated as $Pt3/Y_2O_3$.

Example 14

The catalyst as described in the example 15, 3 wt % Pt/Y2O3 was used for carrying out dehydrogenation of methylcyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner after every 1 sec. The injection frequency and injection pulse with in terms of 0.3 Hz and 10 ms respectively by a frequency regulator. The reaction was carried out in nitrogen atmosphere at a pressure of 1.2 atm. The hydrogen generated was monitored using gas chromatograph for product gas analysis. The conversion efficiency for methylcyclohexane over 3 wt % Pt/Y2O3 catalyst at 350° C. was 98.26% therefore hydrogen storage capacity of 6.1 wt % and 60.92 kg/m3 on volume basis was obtained.

Example 15

A catalyst was synthesized by using $V_2O_5$ as support and $PtCl_4$ as metal precursor with 3 wt % of Pt loading in final product. $V_2O_5$ was dried in oven at 80° C. for 2 h. Platinum loading over $Y_2O_3$ was achieved by wet impregnation method, wherein $PtCl_4$ was taken as 21.11 ml with the molar concentration of 0.02 M. The prepared catalyst was dried in oven at 100° C. The catalyst thus prepared was designated as $Pt3/V_2O_5$.

Example 16

The catalyst as described in the example 17, 3 wt % $Pt/V_2O_5$ was used for carrying out dehydrogenation of methylcyclohexane using a specially designed spray-pulsed rector. A cylindrical reactor was used with an injection nozzle at the top of the reactor. The catalyst was placed at the center of the reactor with arrangement for heating and a temperature controller. The nozzle was placed in such a way to inject atomized spray of reactant over catalysts. The reactant was sprayed in a periodic manner. The injection frequency and injection pulse with in terms of 0.3 Hz and 10 ms respectively by a frequency regulator. The reaction was carried out in nitrogen atmosphere at pressure of 1.2 atm. The hydrogen generated was monitored using gas chromatograph for product gas analysis. The conversion efficiency for methylcyclohexane over 3 wt % $Pt/V_2O_5$ catalyst at 350° C. was 32.06% therefore hydrogen storage capacity of 1.98 wt % and 19.23 $kg/m^3$ on volume basis was obtained.

TABLE 2

Comparative table for various catalysts exhibits hydrogen evaluation rate under same conditions and at temperature of 350° C.

| Catalysts | Maximum Hydrogen evolution rate ($mmol/g_{met}/min$) |
|---|---|
| 3 wt % $Pt/La_2O_3$ | 19.3 |
| 3 wt % $Pt/TiO_2$ | 10.19 |
| 3 wt % $Pt/Al_2O_3$ | 9.44 |
| 3 wt % $Pt/MnO_2$ | 4.41 |
| 3 wt % $Pt/Fe_2O_3$ | 0.047 |
| 3 wt % $Pt/ZrO_2$ | 0.0184 |
| 3 wt % $Pt/CeO_2$ | 1.41 |
| 1 wt % $Pt/La_2O_3$ | 39.81 |
| 1 wt % $Pt/LaNiO_3$ | 17.79 |
| $La_{0.7}Y_{0.3}NiO_3$ | 0.146 |
| 1 wt % $Pt/La_{0.7}Y_{0.3}NiO_3$ | 39.8 |
| 3 wt % $Pt/V_2O5$ | 330.0 |
| 3 wt % $Pt/Y_2O_3$ | 958.92 |

Advantages of the Invention

Main advantage of the present invention include, relatively higher activity of novel catalysts, minimum use of noble metal in the catalyst leading to cost-effective catalysts, relatively high hydrogen storage capacity.

Possible usage of non-fossil fuel based energy namely solar radiation

Simultaneous in-situ generation, storage transport and supply of hydrogen

Pure hydrogen relatively free of COx

Cost effective approach due to reversible catalytic reactions, recyclable reactants and products, and relatively high hydrogen contents (2-8% on weight basis and about 10-62 kg $H_2/m^3$ on volume basis).

Ease of transportation and handling due to high boiling points of cycloalkanes and hydrogenated derivative of aromatic compounds, Avoidance of development of specialized infrastructure and facility by usage of existing infrastructure such as oil tankers and tank lorries for the long-term storage and long-distance transportation of hydrogen in the form of liquid organic hydrides.

We claim:

1. An improved process for delivery of hydrogen, the process comprising:
   dehydrogenating hydrogenated liquid organic compounds using a catalyst in a dehydrogenation reactor to produce hydrogen, the catalyst being heated at a temperature in the range of 120-400° C.;
   removing the hydrogen from the reactor by introducing a carrier gas in the reactor;
   separating the hydrogen with a condenser by cooling to a temperature in the range of 2-50° C., followed by passing the hydrogen through an entrainment separator to release the hydrogen,
   wherein the catalyst is selected from:
   i. M/support wherein metal M is at least one metal selected from the group consisting of Pt, Pd, Rh, Ru, Ir, and Os, and said metal is dispersed on a support, the support is at least one metal oxide selected from the group consisting of $Y_2O_3$, $V_2O_5$ and combinations thereof or;
   ii. M-M'/support wherein metal M is at least one metal selected from the group consisting of Cu, Ag, and Au; metal M' is at least one metal selected from Pt, Pd, Rh, Ru, Ir, Os, Fe, Ni, Re, Mo, W, V, Cr, Co and combinations thereof, and said metals are dispersed on a support, the support is selected from the group consisting of activated carbon, alumina, alumite, zirconia, silica and combinations thereof.

2. The improved process as claimed in claim 1, wherein the hydrogenated liquid organic compounds are in chemically bonded form, capable of storing hydrogen of 2-8 weight percent and 10-62 kg of hydrogen per $m^3$ of volume.

3. The improved process as claimed in claim 2, wherein the hydrogenated liquid organic compounds are selected from the group consisting of cyclohexane, methyl cyclohexane, decalin, 2-propanol and liquid Pi conjugated form of organic compounds.

4. The improved process as claimed in claim 1, wherein the catalyst is heated by using at least one of sources selected from the group consisting of electrical heater, thermic fluid, a renewable energy resource and combination thereof.

5. The improved process as claimed in claim 4, wherein the catalyst is heated by using a renewable energy resource.

6. The improved process as claimed in claim 5, wherein the renewable energy resource is solar concentrator.

7. The improved process as claimed in claim 1, wherein the dehydrogenation reactor used is selected from the group consisting of microchannel reactor, pulse-spray reactor, continuous reactor and column reactor.

8. The improved process as claimed in claim 7, wherein the column reactor has a cross section of rectangular, triangular, elliptical, circular or any irregular shape.

9. The improved process as claimed in claim 1, wherein quantity of M is varied from 2 to 20 wt % of the support weight in M/support metal catalyst and quantity of M is varied from 2 to 20 wt % of the support weight and M' varied from 0.1 to 3 wt % of the support weight in M-M'/support metal catalyst.

10. The improved process as claimed in claim 1, wherein the catalyst used is nanostructured with sizes varying from 3 to 100 nm.

11. The improved process as claimed in claim 1, wherein hydrogen evolution rate using M/support is in the range of 300 to 1000 $mmol/g_{met}/min$ and using M-M'/support is in the range of 10 to 70 $mmol/g_{met}/min$.

12. The improved process as claimed in claim 1, wherein conversion efficiency of the organic compound and hydrogen storage capacity is in the range of 20 to 99% and 1.44 to 6.1 wt % respectively.

13. The improved process as claimed in claim 1, further comprising the step of supplying the hydrogen generated to fuel cells in mobile applications, fuel cells in stationary applications, vegetable oil industry or glass industry.

14. The improved process as claimed in claim 1, wherein the catalyst is the M/support wherein metal M is at least one metal selected from the group consisting of Pt, Pd, Rh, Ru, Ir, and Os, and said metal is dispersed on a support, the support is at least one metal oxide selected from the group consisting of $Y_2O_3$, $V_2O_5$ and combinations thereof.

15. The improved process as claimed in claim 1, wherein the catalyst is the M-M'/support wherein metal M is at least one metal selected from the group consisting of Cu, Ag, and Au; metal M' is at least one metal selected from Pt, Pd, Rh, Ru, Ir, Os, Fe, Ni, Re, Mo, W, V, Cr, Co and combinations thereof, and said metals are dispersed on a support, the support is selected from the group consisting of activated carbon, alumina, alumite, zirconia, silica and combinations thereof.

* * * * *